United States Patent [19]

Kaplan

[11] Patent Number: 5,047,232
[45] Date of Patent: Sep. 10, 1991

[54] NON-AQUEOUS WATERPROOF OIL-BASED COMPOSITIONS AND METHOD OF PREPARING SAME

[75] Inventor: Carl Kaplan, Memphis, Tenn.

[73] Assignee: Schering-Plough Healthcare Products, Inc., Memphis, Tenn.

[21] Appl. No.: 913,172

[22] Filed: Sep. 29, 1986

[51] Int. Cl.$^5$ .................. A61K 7/42; A61K 7/44; A61K 7/48; A61K 9/07

[52] U.S. Cl. .......................... 424/59; 424/60; 514/873; 514/969; 514/972

[58] Field of Search .............. 514/873, 969, 972; 424/59, 60

[56] References Cited

U.S. PATENT DOCUMENTS

| 2,372,807 | 4/1945 | Brown | 514/969 |
| 3,781,417 | 12/1973 | Welters et al. | 514/972 |
| 3,969,193 | 10/1972 | Guglielnetti et al. | 514/972 |
| 4,144,325 | 3/1979 | Voyt | 514/972 |
| 4,335,104 | 6/1982 | Van Cleave | 514/785 |
| 4,466,805 | 8/1984 | Welters et al. | 514/972 X |
| 4,489,057 | 12/1984 | Welters et al. | 514/972 |
| 4,663,155 | 5/1987 | Murray et al. | 514/873 |
| 4,699,781 | 10/1987 | Goupil | 514/873 |

FOREIGN PATENT DOCUMENTS 0088304  5/1983  Japan ................... 514/873

Primary Examiner—Dale R. Ore
Attorney, Agent, or Firm—Thomas D. Hoffman; Gerald S. Rosen; Henry C. Jeanette

[57] ABSTRACT

Non-aqueous waterproof oil-based topical compositions containing one or more water-in-oil emulsifiers having an HLB value of about 1 to about 7, e.g., sorbitan sesquioleate, and at least one cosmetic emollient, e.g., extra heavy mineral oil, as well as methods for making such compositions are disclosed. The waterproof compositions are particularly useful as vehicles for non-aqueous waterproof oil-based topical sunscreen compositions.

12 Claims, No Drawings

NON-AQUEOUS WATERPROOF OIL-BASED COMPOSITIONS AND METHOD OF PREPARING SAME

BACKGROUND OF THE INVENTION

This invention relates to non-aqueous waterproof oil-based topical compositions containing one or more water-in-oil emulsifiers having an HLB value of about 1 to about 7 and at least one cosmetic emollient as well as methods of making such compositions. The waterproof compositions of the present invention are particularly useful as vehicles for sunscreen compositions.

There has long been a need for a cosmetic or medicinal vehicle which is waterproof, i.e., highly resistant to removal by water after exposure to water for 80 minutes.

Barker et al. U.S. Pat. No. 4,177,259 discloses a water-in-oil waterproof makeup comprising (a) a cosmetic emulsion oil, (b) a cosmetic pigment, (c) an emulsifier combination comprising (i) aluminum and/or calcium stearate and (ii) a polyhydric alcohol ester of a liquid fatty acid ester, and (d) water. While the Barker et al. patent discloses that the polyhydric alcohol esters of liquid fatty acids may be, inter alia, trioleate, PEG-22/dodecyl glycol copolymer, PEG-45/dodecyl glycol copolymer, polyglyceryl-3 diisostearate, polyglyceryl-4 oleate, polyglyceryl-4-oleate/PEG-8 propylene glycol cocoate, oleamide DEA, sodium glyceryl oleate phosphate or hydrogenated vegetable glycerides phosphate and at least one cosmetic emollient.

The above described compositions are useful as vehicles for, inter alia, sunscreening agents or oil-soluble ingredients or medicaments to form waterproof topical compositions.

Thus, in a preferred aspect of the present invention, there is provided a non-aqueous waterproof oil-based topical sunscreen composition comprising (1) one or more water-in-oil emulsifiers selected from sorbitan monooleate, sorbitan sesquioleate, sorbitan trioleate, PEG-22/dodecyl glycol copolymer, PEG-45/dodecyl glycol copolymer, polyglyceryl-3-diisostearate, polyglyceryl-4 oleate, polyglyceryl-4 -oleate/PEG-8 propylene glycol cocoate, oleamide DEA, sodium glyceryl oleate phosphate or hydrogenated vegetable glycerides phosphate: and (2) at least one cosmetic emollient; and (3) an effective sunscreening amount of a sunscreening agent.

The present invention also provides a method of preparing a non-aqueous waterproof oil-based topical sunscreen composition comprising one cosmetic emollient and a sunscreening agent which comprises admixing at least one cosmetic emollient, at least one sunscreening agent and one or more water-in-oil emulsifiers selected from sorbitan monooleate, sorbitan sesquioleate, sorbitan trioleate, PEG-22/dodecyl glycol copolymer, PEG-45/dodecyl glycol copolymer, polyglyceryl-3-diisostearate, polyglyceryl-4 oleate, polyglyceryl-4 oleate/PEG-8 propylene glycol cocoate, oleamide DEA, polyglycerol-(4) monooleate or sorbitan sesquioleate, the makeups are water-in-oil emulsions containing aluminum and/or calcium stearate and about 40 to about 85 weight percent water.

Great Britain patent application 1460649 (published Nov. 8, 1974) discloses a waterproof sunscreen composition for the skin comprising a partially esterified polyvinyl butyral polymer containing a major proportion of acetal units and a minor proportion of 4-dimethylaminobenzoate units.

Epstein et al. U.S. Pat. No. 3,506,758 discloses a sunscreening composition having improved adhesion to the skin in the presence of water or perspiration and containing a carrier and an ultra-violet absorbing compound, for example, 3-salicylamido-propyl dimethyl alkyl ammonium halides.

There still is a need for a non-aqueous waterproof oil-based composition suitable for use as a sunscreen composition which will not be easily removed by water. Heretofore, repeated application of even highly substantive sunscreen products have been necessary for persons who swim, remain in the water outdoors for extended periods and/or perspire freely.

SUMMARY OF THE INVENTION

The present invention provides a non-aqueous waterproof oil-based topical composition comprising one or more water-in-oil emulsifiers having an HLB value of from about 1 to about 7, and at least one cosmetic emollient.

The present invention also provides a non-aqueous waterproof oil-based topical composition comprising one or more water-in-oil emulsifiers selected from sorbitan monooleate, sorbitan sesquioleate, sorbitan sodium glyceryl oleate phosphate or hydrogenated vegetable glycerides phosphate, in amounts sufficient to form a non-aqueous waterproof oil-based topical sunscreen composition.

In another aspect of the present invention, there is provided a method of preparing a non-aqueous waterproof oil-based topical sunscreen composition containing at least one cosmetic emollient and a sunscreening agent which comprises incorporating therein one or more water-in-oil emulsifiers having a HLB value of about 1 and about 7.

In still another aspect of the present invention, there is provided a method of preparing a non-aqueous waterproof oil-based topical sunscreen composition containing a mixture of cosmetic emollients comprising mineral oil and other emollients, at least one sunscreening agent and one or more water-in-oil emulsifiers having a HLB value of about 1 to about 7 which comprises admixing the sunscreening agent, one or more of said emulsifiers and the other cosmetic oily ingredients until a homogeneous mixture is formed and admixing said homogenous mixture and mineral oil until a homogenous non-aqueous waterproof oil-based topical sunscreen composition is formed.

Finally, the present invention provides a method of preparing a non-aqueous waterproof oil-based topical sunscreen composition containing a mixture of cosmetic emollients comprising mineral oil and other cosmetic oily ingredients, at least one sunscreening agent and one or more water-in-oil emulsifiers having a HLB value of about 1 to about 7 which comprises (1) admixing said emulsifier and mineral oil until a first mixture is formed, (2) admixing the sunscreening agent and the other cosmetic oily ingredients until a second mixture is formed (3) admixing said first and second substantially clear homogenous mixtures until a non-aqueous waterproof oil-based topical sunscreen composition is formed.

DETAILED DESCRIPTION OF THE INVENTION

We have discovered that non-aqueous waterproof oil-based topical compositions may be prepared by admixing one or more water-in-oil emulsifiers having an HLB value of about 1 to about 7 with at least one cosmetic emollient.

As used herein in reference to the compositions of the present invention, the term "waterproof" means a composition that remains on the skin after exposure to circulating water for at least 80 minutes using the procedures described in "Sunscreen Drug Products for OTC Human Use", Federal Register, Vol. 43, Aug. 25, 1978, Part 2, pp 38206-38269.

As used herein in reference to the compositions of the present invention, the term "non-aqueous" means substantially water-free. While water is not intentionally added to the compositions of the present invention, no attempt has been made to exclude or remove water from the ingredients used in the compositions of the present invention.

As used herein in reference to the water-in-oil emulsifiers, the term "HLB value" means the hydrophilic-lipophilic balance. The HLB value has been used by those skilled in the emulsion art for selecting emulsifiers useful for preparing inter alia water-in-oil emulsions. See U.S. Pat. No. 4,177,259 and references cited therein. Even though the term "water-in-oil emulsifiers" is used in reference to the compositions of the present invention, the compositions are oil-based and non-aqueous; no emulsions are formed.

Typical suitable water-in-oil emulsifiers having an HLB value about 1 to about 7 include sorbitan monooleate, sorbitan sesquioleate, sorbitan trioleate, PEG-22/dodecyl glycol copolymer, PEG-45/dodecyl glycol copolymer, polyglyceryl-3-diisostearate, polyglyceryl-4 oleate, polyglyceryl-4 oleate/PEG-8 propylene glycol cocoate, oleamide DEA, sodium glyceryl oleate phosphate and hydrogenated vegetable glycerides phosphate.

The water-in-oil emulsifiers useful in the present invention are non-ionic and may be liquid or solid at room temperature and should be compatible, i.e., soluble and stable with the cosmetic emollients. Preferred water-in-oil emulsifiers have a HLB value of less than about 5, e.g., sorbitan sequioleate (HLB value is 3.7), sorbitan monooleate (HLB value is 4.3) and sorbitan trioleate (HLB value is 1.8).

Conveniently, the quantity of water-in-oil emulsifier found useful in the compositions of the present invention is in the range of about 1 to about 5 weight percent of composition.

Typical suitable cosmetic emollients include mineral oil, having a viscosity in the range of 50 to 500 SUS, lanolin oil, coconut oil, cocoa butter, olive oil, almond oil, macadamia nut oil, aloe extract, jojoba oil, safflower oil, corn oil, liquid lanolin, cottonseed oil and peanut oil.

Conveniently, extra heavy mineral oil having a viscosity of 360-390 SUS and available from Witco Chemical Corp. Sonneborn Div., under the tradename Primol-54 and at least one other and preferably several of the other cosmetic emollients or oily ingredients, listed above are incorporated into the compositions of the present invention. The use of extra heavy mineral oil in the compositions and methods of the present invention is preferred but not critical; any mineral oil having a viscosity in the range of 50 to 500 SUS may also be used in place thereof.

Other typical suitable cosmetic emollients include Purcellin oil, perhydrosqualene, castor oil, polybutene, odorless mineral spirits, sweet almond oil, avocado oil, calophyllum oil, ricin oil, vitamin E acetate, olive oil, silicone oils such as dimethylpolysiloxane and cyclomethicone, linolenic alcohol, oleyl alcohol, the oil of cereal germs such as the oil of wheat germ, isopropyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other typical suitable cosmetic emollients which are solids or semi-solids at ambient temperatures may be used if admixed with mineral oil in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate.

The waterproof sunscreen compositions of the present invention all contain a sunscreening effective amount of one of an oil-soluble sunscreening agent of the UV-B type or a combination of the UV-B and UV-A types. UV-A type sunscreening agent protect against long wavelength actinic radiation in the 320 to 400 nm range and UV-B sunscreening agents protect against shorter wave length, actinic radiation in the 290-320 nm range.

Typical suitable UV-B type sunscreening agents include substituted para-aminobenzoates, e.g., octyl viscosity in the range of 50 to 500 SUS may also be used in place thereof.

Other typical suitable cosmetic emollients include Purcellin oil, perhydrosqualene, castor oil, polybutene, odorless mineral spirits, sweet almond oil, avocado oil, calophyllum oil, ricin oil, vitamin E acetate, olive oil, silicone oils such as dimethylpolysiloxane and cyclomethicone, linolenic alcohol, oleyl alcohol, the oil of cereal germs such as the oil of wheat germ, isopropyl palmitate, isopropyl myristate, butyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other typical suitable cosmetic emollients which are solids or semi-solids at ambient temperatures may be used if admixed with mineral oil in amounts sufficient to provide liquid topical compositions. Such solid or semi-solid cosmetic emollients include hydrogentated lanolin, hydroxylated lanolin, acetylated lanolin, petrolatum, isopropyl lanolate, cetyl myristate, myristyl myristate, myristyl lactate, cetyl alcohol, isostearyl alcohol and isocetyl lanolate.

The waterproof sunscreen compositions of the present invention all contain a sunscreening effective amount of one of an oil-soluble sunscreening agent of the UV-B type or a combination of the UV-B and UV-A types. UV-A type sunscreening agent protect against long wavelength actinic radiation in the 320 to 400 nm range and UV-B sunscreening agents protect against shorter wave length, actinic radiation in the 290-320 nm range.

Typical suitable UV-B type sunscreening agents include substituted para-aminobenzoates, e.g., octyl dimethyl PABA, available from Van Dyk & Co., Inc., Belleville, N.J. 07109 under the tradename Escalol 507 and usually present in the range of about 1.5 to 8.0 weight percent, alkyl esters of para-methoxycinnamate, e.g., octyl para-methoxycinnamate, available from Givaudan Corp., Clifton, N.J. 07104 under the tradename Parsol MCX and usually present in the range of about 1.5–7.5 weight percent, certain esters of salicylic acid, e.g., homomethyl salicylate, usually in the range of about 4.0 to 15 weight percent or octyl salicylate, usually in the range of about 3 to 5 weight percent. (All weight precents are weight percent of total sunscreen composition).

Typical suitable UV-A type sunscreening agents include benzophenone-3 usually present in the composition in the range of about 0.5 to 6 percent and available from American Cyanamid Co., Wayne, N.J. 07470 under the tradename Spectra-Sorb UV-9 and benzophenone-8, usually present in the composition in the range of about 0.5 to 3 weight percent and available from American Cyanamid Co. under the tradename Spectra-Sorb UV-24.

The compositions of the present invention may also contain perfumes, preservatives, dyes, softeners, and antioxidants.

Typical suitable antioxidants include propyl, octyl and dodecyl esters of gallic acid, butylated hydroxyanisole (usually as a mixture of ortho and meta isomers), butylated hydroxytoluene and nordihydroguaiaretic acid.

Typical suitable preservatives include the lower alkyl esters of para-hydroxybenzoates (paraben) especially, methyl paraben, ethyl paraben, propyl paraben, butyl paraben, isobutyl paraben and mixtures thereof, and benzoic acid.

The compositions of the present invention adaptable for use as cosmetics also include one or more organic dyes, which are generally dissolved in an oily vehicle.

Typical suitable dyes employed in the cosmetic compositions of the present invention are the U.S. Government certified colors, both Drug and Cosmetic grade and Food, Drug and Cosmetic grade, e.g., D & C reds, oranges, yellows and blues.

Typical suitable perfumes include any oil soluble perfume or mixture of perfumes well known to those skilled in the art.

The non-aqueous waterproof oil-based topical compositions of the present invention may be prepared by admixing, in one container, one or more water-in-oil emulsifiers having a HLB value of about 1 to about 7 with at least one cosmetic emollient, e.g., mineral oil and, optionally perfumes, preservatives, and antioxidants until a homogenous mixture is produced (hereinafter Method A).

Non-aqueous waterproof oil-based topical sunscreen compositions containing at least one cosmetic emollient, e.g., mineral oil and a sunscreening agent may also be prepared by admixing a sunscreening agent, with at least one emollient and incorporating therein one or more water-in-oil emulsifiers having a HLB value of about 1 to about 7 (hereinafter Method B).

The specific sunscreening effective amount of each sunscreening agent of the UV-B and UV-A types is listed hereinabove.

The water-in-oil emulsifiers, incorporated in the compositions of the present invention in the amount of about 1 to about 5 percent by weight of the total composition, are commercially available. For example, sorbitan monooleate, sorbitan sesquioleate and sorbitan trioleate are available from ICI Americas, Inc., Wilmington, Del. 19897 under the tradenames Arlacel 80, Arlacel 83 and Arlacel 85, respectively.

PEG-22/dodecyl glycol copolymer and PEG-45/dodecyl glycol copolymer are available from Akzo Chemie B.V., Amersfort, Netherlands under the tradenames Elfacos ST37 and Elfacos ST9, respectively. Polyglyceryl-3-diisostearate is available from Emery Industries, Linden, N.J. 07036. Polyglyceryl-4 oleate/PEG-8 propylene glycol cocoate is available from Van Dyk & Co., Inc., Belleville, N.J. 07109 under the tradename Emulsynt 1055. Polyglyceryl-4 oleate, oleamide DEA, sodium glyceryl oleate phosphate and hydrogenated vegetable glycerides phosphate are available from Witco Chemical Corp., Organic Div., New York, N.Y. 10017 under the tradenames Witconol 14, Witcomul 4120, Emphos D70-30C and Emphos F27-85, respectively.

In a preferred aspect of the present invention (hereinafter Method C), a non-aqueous waterproof oil-based topical sunscreen composition may be prepared by admixing a sunscreening effective amount of at least one sunscreening agent, one or more of the water-in-oil emulsifiers and the cosmetic emollients or oily ingredients (except the extra heavy mineral oil) until a homogeneous admixture is formed. Normally, a stainless steel pot equipped with a stirrer and heated to about 180° F. is used. Stirring and heating are maintained until all the solids, if present, dissolve and a homogeneous admixture is formed. The homogeneous admixture is added to the extra heavy mineral oil containing e.g., perfume(s) and stirring and heating is maintained until a homogeneous non-aqueous waterproof oil-based topical sunscreen composition is formed. The order of mixing is not critical, but normally the homogeneous admixture containing the sunscreening agent and one or more water-in-oil emulsifiers has a smaller volume and thus is more easily added to the larger volume i.e. extra heavy mineral oil.

In another preferred aspect of the present invention, a mixture of two sunscreens, one of the UV-B type, e.g., octyl dimethyl PABA or octyl paramethoxycinnamate in the amount of about 5 weight percent and one of the UV-A type, e.g., benzophenone-3, in the amount of about 0.8 weight percent is admixed with about 2 weight percent of one of the preferred water-in-oil emulsifiers, e.g., sorbitan monooleate, sorbitan sesquioleate or soribtan trioleate and about 0.1 to about 10 weight percent preferably about 0.8 to 4 weight percent (basis total composition) of a mixture of various cosmetic emollients, e.g., lanolin, coconut oil, cocoa butter, almond oil, about 0.1 to 0.5 weight percent (basis total composition) of one or more preservatives, e.g., benzoic acid or one or more of the parabens. The homogeneous mixture so formed is added to the extra heavy mineral oil containing inter alia, a small amount of perfume or fragrance. Normally, the amount of extra heavy mineral oil is in the range of about 80 to 96 weight percent, preferably 87 to 94 weight percent of the total composition.

The non-aqueous waterproof oil-based topical sunscreen composition of the present invention may be clear (i.e., non-translucent and non-opaque), translucent, i.e., hazy or slightly cloudy or even opaque. While a clear sunscreen composition is cosmetically a more elegant product which may be placed in a see-through container, hazy or slightly cloudy non-aqueous oil-based compositions (as well as clear or even opaque compositions), prepared by methods A, B or C hereinabove, are useful as non-aqueous waterproof oil-based topical sunscreen compositions.

Clear non-aqueous waterproof oil-based sunscreen compositions containing any of the water-in-oil emulsifiers listed above, except sorbitan monooleate or sorbitan sesquioleate, may be prepared using methods A, B or C. Clear non-aqueous waterproof oil-based sunscreen compositions containing sorbitan monooleate or sorbitan sesquioleate are formed using method B. When sorbitan monooleate and sorbitan sesquioleate were admixed using methods A or C, hazy and slightly cloudy compositions useful as waterproof oil-based sunscreen compositions were formed.

Surprisingly, it was discovered that non-aqueous waterproof oil-based sunscreen compositions containing sorbitan monooleate or sorbitan sesquioleate could be formed as a clear homogeneous mixture by using the following method (hereinafter Method D). At least one of the water-in-oil emulsifiers, e.g., sorbitan monooleate or sorbitan sesquioleate which formed a hazy or slightly cloudy product by use of Methods A, B or C is admixed in one container with the extra heavy mineral oil until a first homogeneous mixture is formed. To a second container equipped with a stirrer and heating means, there is added a mixture of cosmetic emollients the preservatives (0.1 to 0.5 weight percent) and at least one sunscreening agent (normally a mixture of one UV-B type and one UV-A type). The stirring and heating (up to about 180° F.) are continued until a second homogeneous mixture is formed. The first and second homogeneous mixtures are admixed while stirring is continued until a homogeneous mixture is formed. Normally, the second homogeneous mixture at a temperature of about 180° F. is added to the first homogeneous mixture which is usually at ambient temperature. The perfume or fragrance mixture is thereafter added to form a clear non-aqueous waterproof oil-based topical sunscreen composition.

Definitions and suppliers of the ingredients used in the following illustrative examples may be found in the CTFA Cosmetic Ingredient Dictionary, published by the Cosmetic, Toiletry and Fragrance Association, Inc., 1110 Vermont Avenue, NW, Washington, D.C. 20005, Third Edition, 1982.

EXAMPLE 1

|  | Parts by Weight |
| --- | --- |
| Part A | |
| Extra Heavy Mineral Oil | 12,285 |
| Sorbitan Sesquioleate | 280 |
| Part B | |
| Lanolin | 70 |
| Coconut Oil | 70 |
| Cocoa Butter | 70 |
| Olive Oil | 70 |
| Almond Oil | 70 |
| Macadamia Nut Oil | 35 |
| Aloe Extract | 28 |
| Jojoba Oil | 28.0 |
| Vitamin E Acetate | 14.0 |
| Benzoic Acid | 28.0 |
| Benzophenone-3 | 112 |
| Octyl Dimethyl PABA | 700 |
| Part C | |
| Coconut fragrance | 140 |
| Total: | 14,000 |

Add Part A to a pot and mix until a clear homogeneous mixture is formed. In another pot, heat Part B to 180° F. with stirring until all solids dissolve. Add Part B at 180° F. to Part A at room temperature. Stir until a clear homogeneous mixture is formed. Add Part C. Stir until a clear homogeneous mixture is formed.

The sunscreening composition of Example 1 was a waterproof SPF 4 product when tested on twenty-five human subjects in accordance with the procedures described in "Sunscreen Drug Products for OTC Human Use", Federal Register, Vol. 43, Aug. 25, 1987, Part 2, pp. 38,206–38,269.

EXAMPLE 2

|  | Parts by Weight |
| --- | --- |
| Part A | |
| Extra Heavy Mineral Oil | 911.5 |
| Sorbitan Sesquioleate | 20.0 |
| Part B | |
| Lanolin | 5.0 |
| Coconut Oil | 5.0 |
| Cocoa Butter | 5.0 |
| Olive Oil | 5.0 |
| Almond Oil | 5.0 |
| Macadamia Nut Oil | 2.5 |
| Aloe Extract | 2.0 |
| Jojoba Oil | 2.0 |
| Vitamin E Acetate | 1.0 |
| Benzoic Acid | 2.0 |
| Octyl Dimethyl PABA | 30.0 |
| Part C | |
| Perfume | 4.0 |
| Total: | 1,000 |

Follow the procedure of Example 1 to admix the ingredients in Parts A, B and C to obtain a clear homogeneous waterproof sunscreen composition listed above.

EXAMPLES 3–12

EXAMPLE 3

|  | Parts by Weight |
| --- | --- |
| Part A | |
| Sorbitan Monooleate | 2.0 |
| Octyl Dimethyl PABA | 5.0 |
| Benzophenone-3 | 0.8 |
| Benzoic Acid | 0.2 |
| Lanolin Oil | 0.5 |
| Coconut Oil | 0.5 |
| Cocoa Butter | 0.5 |
| Olive Oil | 0.5 |
| Almond Oil | 0.5 |
| Macadamia Nut Oil | 0.25 |
| Aloe Extract | 0.2 |
| Jojoba Oil | 0.2 |
| Vitamin E Acetate | 0.1 |
| Part B | |
| Extra Heavy Mineral Oil | 87.75 |
| Coconut fragrance | 1.0 |
| Total: | 100.00 |

Admix all ingredients in Part A in a stainless steel pot until a homogeneous mixture is formed. Add mixture of Part A to Part B and stir. A slightly hazy sunscreen composition is formed.

To prepare the sunscreen compositions of Example 4–12, follow the procedure of Example 3 except substitute for sorbitan monooleate an equivalent quantity of each of the following water-in-oil emulsifiers: sorbitan sesquioleate (Example 4); PEG-22/dodecyl glycol copolymer (Example 5); PEG-45/dodecyl glycol copolymer (Example 6); oleamide DEA (Example 7); sorbitan trioleate (Example 8); polyglyceryl-3 diisostearate (Example 9); polyglyceryl-4 oleate (Example 10); sodium glyceryl oleate phosphate (Example 11); and hydrogenated vegetable glycerides phosphate (Example 12).

Sunscreen compositions of Example 5-12 were clear. The sunscreen composition of Example 4 was cloudy but a clear sunscreen composition would be formed if the procedure of Example 1 (method D) were used.

EXAMPLES 13-20

EXAMPLE 13

| | Parts by Weight |
|---|---|
| Part A | |
| Sorbitan Trioleate | 2.0 |
| Octyl-para-Methoxycinnamate | 5.0 |
| Benzophenone-3 | 0.8 |
| Benzoic Acid | 0.2 |
| Lanolin Oil | 0.5 |
| Coconut Oil | 0.5 |
| Cocoa Butter | 0.5 |
| Olive Oil | 0.5 |
| Almond Oil | 0.5 |
| Macadamia Nut Oil | 0.25 |
| Aloe Extract | 0.2 |
| Jojoba Oil | 0.2 |
| Vitamin E Acetate | 0.1 |
| Part B | |
| Extra Heavy Mineral Oil | 87.75 |
| Coconut fragrance | 1.0 |
| Total: | 100.0 |

Follow the procedure of Example 3 to admix the ingredients in Parts A and B of Example 13 to prepare a substantially clear homogeneous oil-based waterproof sunscreen composition.

Prepare the sunscreen compositions of Examples 14-20 by following the procedure of Example 13 except substitute for sorbitan trioleate an equivalent amount of each of the following water-in-oil emulsifiers: polyglyceryl-4 oleate (Example 14); polyglyceryl-4-oleate and PEG-8 propylene glycol cocoate (Example 15); polyglyceryl-3-diisostearate (Example 16); oleamide DEA (Example 17); PEG-22/dodecyl glycol copolymer (Example 18); PEG-45/dodecyl glycol copolymer (Example 19); and sodium glyceryl oleate phosphate (Example 20).

What is claimed is:

1. A non-aqueous waterproof oil-based topical sunscreen composition comprising about 1 to about 5 weight percent of one or more water-in-oil emulsifiers having an HLB value of about 1 to about 7, at least one cosmetic emollient, and a sunscreening effective amount of a sunscreening agent.

2. A non-aqueous waterproof oil-based topical composition of claim 1 which further comprises a preservative.

3. A non-aqueous waterproof oil-based topical sunscreen composition comprising (1) about 1 to about 5 weight percent of one or more water-in-oil emulsifiers selected from sorbitan monooleate, sorbitan sesquioleate, sorbitan trioleate, PEG-22/dodecyl glycol copolymer, PEG-45/dodecyl glycol copolymer, polyglyceryl-3 diisostearate, polyglyceryl-4 oleate, polyglyceryl-4 oleate/PEG-8 propylene glycol cocoate, oleamide DEA, sodium glyceryl oleate phosphate or hydrogenated vegetable glycerides phosphates; (2) at least one emollient; and (3) an effective sunscreening amount of a sunscreening agent.

4. A non-aqueous waterproof oil-based topical sunscreen composition of claim 3 wherein said emulsifier is sorbitan monooleate.

5. A non-aqueous waterproof oil-based topical sunscreen composition of claim 3 wherein said emulsifier is sorbitan trioleate.

6. A non-aqueous waterproof oil-based topical sunscreen composition of claim 3 wherein said emulsifier is sorbitan sesquioleate.

7. A method of preparing a non-aqueous waterproof oil-based topical sunscreen composition containing at least one cosmetic emollient and a sunscreening agent which comprising admixing at least one cosmetic emollient and at least one sunscreening agent and about 1 to about 5 weight percent of one or more water-in-oil emulsifiers selected from sorbitan monooleate, sorbitan sesquioleate, sorbitan trioleate, PEG-22/dodecyl glycol copolymer, PEG-45/dodecyl glycol copolymer, polyglyceryl-3 diisostearate, polyglyceryl-4 oleate, polyglycertl-4 oleate/PEG-8 propylene glycol cocoate, oleamide DEA, sodium glyceryl oleate phosphate or hydrogenated vegetable glycerides phosphates in amounts sufficient to form a non-aqueous waterproof oil-based topical sunscreen composition.

8. A method of claim 7 wherein said emulsifier is sorbitan monooleate.

9. A method of claim 7 wherein said emulsifier is sorbitan sesquioleate.

10. A method of claim 7 wherein said emulsifier is sorbitan trioleate.

11. A method of preparing a non-aqueous waterproof oil-based topical sunscreen composition containing at least one cosmetic emollient and a sunscreening agent which comprises incorporating therein about 1 to about 5 weight percent of one or more water-in-oil emulsifiers having a HLB value of about 1 to about 7.

12. A non-aqueous waterproof oil-based topical sunscreen composition of claim 3 which further comprises a preservative.

* * * * *